(12) United States Patent
Islam

(10) Patent No.: US 8,062,407 B2
(45) Date of Patent: Nov. 22, 2011

(54) HOUSEHOLD MICROWAVE-MEDIATED CARBOHYDRATE-BASED PRODUCTION OF SILVER NANOMATERIALS

(75) Inventor: M. Rafiq Islam, Maryville, MO (US)

(73) Assignee: Northwest Missouri State University, Maryville, MO (US)

( * ) Notice: Subject to any disclaimer, the term of this patent is extended or adjusted under 35 U.S.C. 154(b) by 363 days.

(21) Appl. No.: 12/343,174

(22) Filed: Dec. 23, 2008

(65) Prior Publication Data

US 2010/0154591 A1   Jun. 24, 2010

(51) Int. Cl.
*B22F 9/24*   (2006.01)
(52) U.S. Cl. ............. 75/345; 75/371; 977/896; 977/957
(58) Field of Classification Search ...................... 75/345
See application file for complete search history.

(56) References Cited

U.S. PATENT DOCUMENTS

| | | | |
|---|---|---|---|
| 2006/0065075 A1* | 3/2006 | Chang et al. | 75/371 |
| 2007/0101824 A1* | 5/2007 | Drzal et al. | 75/345 |
| 2008/0058627 A1* | 3/2008 | Hernandez | 600/365 |

OTHER PUBLICATIONS

Mallikarjuna, N. et al., Microwave-Assisted Shape-Controlled Bulk Synthesis of Noble Nanocrystals and Their Catalytic Properties, Crystal Growth and Design, vol. 7, No. 4, pp. 686-690, published Feb. 22, 2007.*

* cited by examiner

*Primary Examiner* — George Wyszomierski
(74) *Attorney, Agent, or Firm* — Husch Blackwell LLP

(57) ABSTRACT

A relatively simple and inexpensive method for the synthesis of silver nanoparticles within a short period of time using a household microwave or the like is provided. The energy needed to heat the synthesis reaction is minimized and the organic reducing reagents of the prior art are replaced with natural products such as purified carbohydrates (e.g., glucose, sucrose, fructose, galactose, ribose, lactose) or their readily available and inexpensive forms (e.g., high fructose corn syrup, sucrose syrup). The resulting nanoparticles are purified from the remaining silver ion which is then recaptured for the safe disposal of the waste reaction mixture.

18 Claims, 11 Drawing Sheets

A

B

HOUSEHOLD MICROWAVE-MEDIATED CARBOHYDRATE-BASED PRODUCTION OF SILVER NANOMATERIALS

BACKGROUND OF THE INVENTION

Nanoscience, sometimes called "nanotechnology" or "nanotech," refers to a field focused on the control of matter on an atomic and molecular scale. Generally, nanoscience deals with structures 100 nanometers or smaller, and involves developing materials or devices within that size. The potential applications for nanotechnology are extremely diverse and include, for example, extensions of conventional device physics, new approaches based upon molecular self-assembly, development of new materials with dimensions on the nanoscale, prolongation of cell viability and biological labeling to study intracellular trafficking and organelle functions and other everyday applications such as photography, reaction catalysis, optoelectronics and information storage. The potential to create many new materials and devices with wide-ranging applications, such as in medicine, electronics, and energy production, renders nanoscience a popular field of study. However, nanotechnology raises many of the same issues that come with the introduction of any new technology including concerns about the toxicity and environmental impact of nanomaterials.

Ionic silver (such as silver nitrate) has long been known as an antimicrobial or antifungal agent with the power to kill bacteria and other germs. In fact, ancient Greeks and Romans frequently used silver as an antiseptic in the pre-antibiotic era and even kept their liquids free from contamination by placing the liquids in silver jars. However, ionic silver was abandoned for such uses due to its cytotoxicity and adverse effect on human and animal health and has been limited to non-health related uses such as photography. Recently, however, a number of studies have reported the efficacy of silver nanoparticles as an antimicrobial against bacteria such as E. coli and even against viruses such as the Human Immunodeficiency Virus and it has been shown that silver particles are 100 times more effective than silver salts as antiseptics. It would therefore be desirable to prepare silver nanoparticles or silver-alloy nanoparticles to maximize the antimicrobial properties of silver. Moreover, recent studies have shown that, in proper concentrations, silver nanoparticles are not dangerous to humans when used externally.

Various methods have been employed for the synthesis of nanoparticles of metallic origins including co-precipitation methods in aqueous solutions, electrochemical methods, aerosol, reverse microemulsion, chemical liquid deposition, photochemical reduction, chemical reduction in solution, and UV radiation. For example, conventional methods have included the reduction of $Ag^+$ with sodium borohydride, aldehyde, hydrazine, or phenylhydrazine with alkylamine as reductants and have also included synthesis via a solvothermal process. However, solvothermal synthesis typically relies on multiple reagents and requires controlled conditions which can be tedious and troublesome.

Moreover, all of these methods have limitations in controlling the particle size and production of particles on an industrial scale. Capping reagents such as poly(N-vinyl-2-pyrrolidone) (PVP) are commonly used to regulate the size and morphology of the nanoparticles synthesized. However, the strong hydrophobicity of many capping reagents requires an organic solvent such as acetone, methanol, or toluene in order to counteract the hydrophobicity. Chelating agents have also been used for controlling the aggregation of nanoparticles, but many of these agents and the reagents described herein-above are toxic and therefore harmful to humans and the environment. In order to eliminate the use of such hazardous organic chemicals, a hydrothermal process has been developed which involves Ag NP synthesis by reduction of $Ag^+$ using β-D-glucose inside the nanoscopic template formed by a starch. However, this method requires at least twenty hours of incubation and uses a starch as stabilizing reagent. A costly microwave-digestion system-assisted synthesis using polyol has also been reported as accelerating the liquid-phase reaction in synthesizing nanoparticles.

Thus, most of the currently available methods require the use of hazardous organic solvents, stabilizers, capping reagents, the purging of reaction vessels with inert gases, and/or prolonged incubation, even with the use of expensive microwave synthesizers. In addition, the presence of stabilizers and capping reagents interferes with the purification of nanoparticles and reduces the yield thereby raising the risk of presence of silver ion ($Ag^+$) as a contaminant. Moreover, the use of organic reagents, organic solvents, organic-aqueous mixtures, organic capping reagents, and the disposal of unreacted silver ion result in increased, costly, and hazardous waste. It is therefore desirable to provide a method of preparing silver nanoparticles that does not include the use or the production of hazardous materials and that is less costly to produce.

SUMMARY OF THE INVENTION

There is therefore provided in the practice of the invention, a relatively simple and inexpensive method for the synthesis of silver nanoparticles within a short period of time using a household microwave or the like. The energy needed to heat the synthesis reaction is minimized and the organic reducing reagents of the prior art are replaced with natural products such as purified carbohydrates (e.g., glucose, sucrose, fructose, galactose, ribose, lactose) or their readily available inexpensive forms (e.g., high fructose corn syrup, sucrose syrup). The resulting nanoparticles are purified from the remaining silver ion which is then recaptured for the safe disposal of the waste reaction mixture.

As used herein, the chemical symbols are based on International Union of Pure and Applied Chemistry (IUPAC) systematic names. For example, the symbols Ag, Au, Co, and Ni correspond to silver, gold, cobalt and nickel, respectively.

Certain embodiments of the invention are outlined above in order that the detailed description thereof may be better understood, and in order that the present contributions to the art may be better appreciated. There are, of course, additional embodiments of the invention that will be described below and which will form the subject matter of the claims appended hereto.

In this respect, it is to be understood that the invention is not limited in its application to the details of construction and to the arrangements of the components set forth in the following description. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention. Though some features of the invention may be claimed in dependency, each feature has merit when used independently.

BRIEF DESCRIPTION OF THE SEVERAL VIEWS OF THE DRAWING

Further features of the present invention will become apparent to those skilled in the art to which the present invention relates from reading the following description with reference to the accompanying drawings that form a part of the specification and that are to be read in conjunction therewith, in which.

DETAILED DESCRIPTION OF THE INVENTION

Figure 1A:
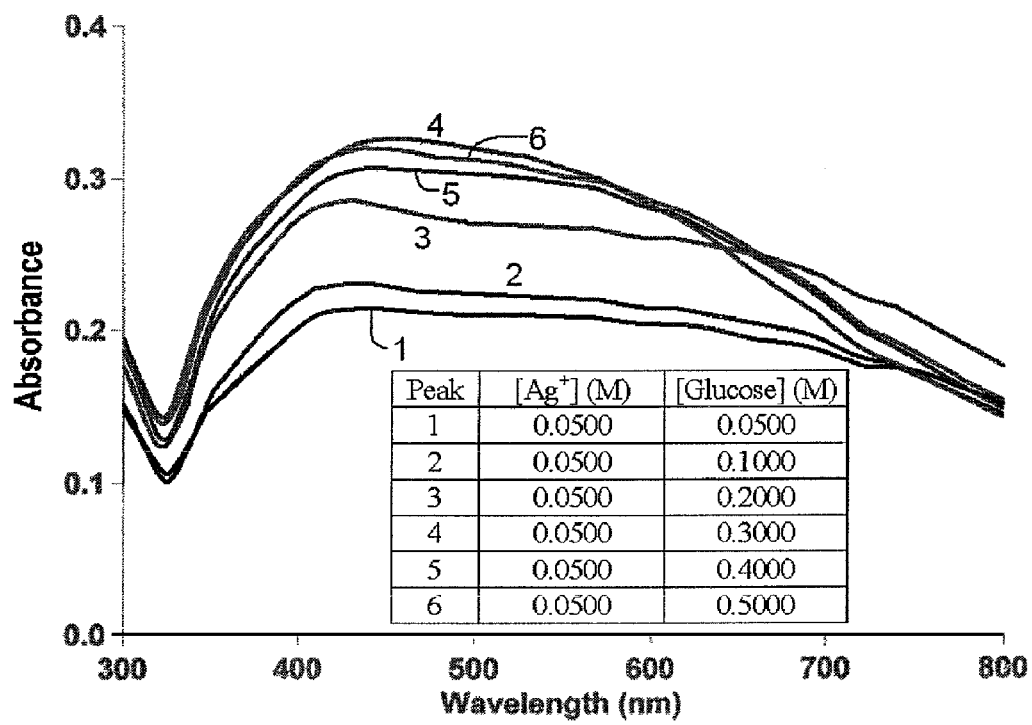
FIG. 1A is a graphical representation of the UV-visible spectra of colloidal mixtures containing silver nanoparticles wherein the $\lambda_{max}$ is observed at 452 nm in accordance with one embodiment of the present invention.

There is provided herein a household microwave-mediated carbohydrate-based method of producing silver nanomaterials. In accordance with certain embodiments of the present invention, the method hereof generally includes admixing a quantity of at least one carbohydrate reductant and a quantity of at least one silver ion source in an aqueous solution in accordance with the following reaction formula:

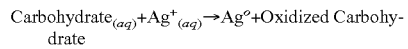

Carbohydrate$_{(aq)}$+Ag$^+_{(aq)}$→Ag$^o$+Oxidized Carbohydrate

It will be appreciated by those skilled in the art that the amount or concentration of carbohydrate reductant and/or silver ion source used may vary depending upon the size of silver nanoparticles desired to be produced. Generally, from about a 1:1 to about a 1:10 molar excess, more preferably from about a 1:2 to 1:8 molar excess, and most preferably about a 1:5 molar excess, of carbohydrate to silver ion may be used. So, for example, a reaction containing about 0.05 M of AgNO$_3$ would correspondingly contain about 0.5 M of a carbohydrate reductant. As used herein, a reductant refers to molecules used to reduce a metal ion. Preferred carbohydrate (or sugar) reductants for use in the present invention include, but are not limited to, polyhydroxy aldehydes or ketones, the substantially pure form of glucose, sucrose, lactose, maltose, sorbose, fructose, galactose, ribose, and mixtures thereof or the more readily available forms thereof including high fructose corn syrup, sucrose syrup, and dextrose, and mixtures thereof. In an alternate embodiment, the method of the present invention may also be used for the detection and quantification of sugars and, in particular, sucrose because it is considered to be non-reducing compared to the carbohydrate reductants discussed hereinabove. Sucrose also produces a distinctive color with a $\lambda_{max}$ of 430 nm which allows for relatively quick measurement of its concentration in solution. The method may also be used to detect and measure the concentration of other sugars such as ribose, lactose, and fructose.

The preferred silver ion source for use in the present invention is silver nitrate. However, it will be appreciated by those skilled in the art that other silver ion sources may also be used without departing from the scope of the present invention. Moreover, it will be appreciated that the method of the present invention may also be used to produce nanoparticles from gold, cobalt, and nickel. It will also be appreciated that any suitable source or form of water may be used to prepare the aqueous solution hereof including, but not limited to, autoclaved reverse osmosis water, deionized water, and mixtures thereof.

Next, the reaction mixture hereof is heated to a temperature of from about 50-120° C., more preferably from about 60-100° C. and, most preferably from about 70-90° C. In particularly preferred embodiment of the present invention, the reaction mixture is heated until it begins boiling at about 100° C. A particularly preferred heat source is a standard household or commercial microwave oven or the like. As used herein, a microwave oven or microwave is a kitchen appliance that cooks or heats food or other objects by dielectric heating. This is accomplished by using microwave radiation to heat water and other polarized molecules within the food. This excitation is fairly uniform, leading to food being adequately heated throughout (except in thick objects), a feature not seen in any other heating technique. Typical microwaves have a power output of from about 400-1200 watts; however, it will be appreciated that any microwave oven suitable for use in the present invention may be used without departing from the scope hereof. Because of the high power output of a microwave, the reaction mixture hereof is typically heated to boiling by using the highest temperature setting on the microwave and microwaving the reaction mixture for a time period of from about 1-60 seconds, more preferably from about 1-30 seconds and, most preferably, 5-20 seconds.

After reaching boiling temperature, the reaction mixture is removed from the heat source and the reaction mixture is typically separated into its component parts by centrifugation wherein the silver nanoparticles form a precipitate and unreacted carbohydrate reductant and unreacted silver nitrate form the supernatant. Following separation and removal from the separated reaction mixture, the resulting silver nanoparticles hereof may be washed at least once and then resuspended in aqueous solution to a desired concentration. As used herein, a nanoparticle or nanocolloid refers to a particle that is less than about or substantially equal to 200 nm, more preferably in the range of from about 20-100 nm, and most preferably in the range of from about 10-50 nm.

After collecting the silver nanoparticles, the supernatant from the reaction mixture containing unreacted carbohydrate reductants and silver nitrate may be treated further with carbohydrate solution to synthesize more silver nanoparticles and dispose of the waste. Alternatively or in addition, the supernatant may also be processed to recover silver ions. In this aspect of the inventive method, about a 5- to 10-fold molar excess of sodium chloride was added to the supernatant which caused over 95% precipitation of the silver ion in the unreacted supernatant as silver chloride (AgCl). The silver chloride may then be collected by centrifugation, dried and processed with one of the available methods to recover silver ions. The remaining supernatant is no longer hazardous and safe to dispose. After collecting the silver chloride, the remaining supernatant may be then re-treated with a 5-fold molar excess of sodium chloride to ensure that no remaining silver ions precipitate out and to ensure that the supernatant is no longer hazardous and safe to dispose. The collected sodium chloride may then be dried and processed to recover the silver ions.

The following examples are offered by way of illustration and not by way of limitation. It will be appreciated by those of ordinary skill in the art that any of the apparatus used herein may be substituted with other apparatus suitable for use in the methods of the present invention.

EXAMPLES

Example 1

0.05 M of silver nitrate and 0.5 M carbohydrate reductant (glucose) were admixed in autoclaved reverse osmosis water. Immediately after mixing, the reaction mixture was microwaved in a standard household microwave oven at the highest temperature setting for about eight (8) seconds until the mixture began boiling. The reaction mixture was then placed in a centrifuge for ten minutes at 10,000 rpm in order to separate the resulting silver nanoparticles from the supernatant containing the unreacted carbohydrate reductant and unreacted silver nitrate. After separation and collection, the silver nanoparticles were washed twice with autoclaved reverse osmosis water and resuspended in autoclaved reverse osmosis water until the desired concentration was reached. The remaining supernatant was treated with an excess of sodium chloride and processed to recover silver ions therefrom.

Example 2

Figure 2:
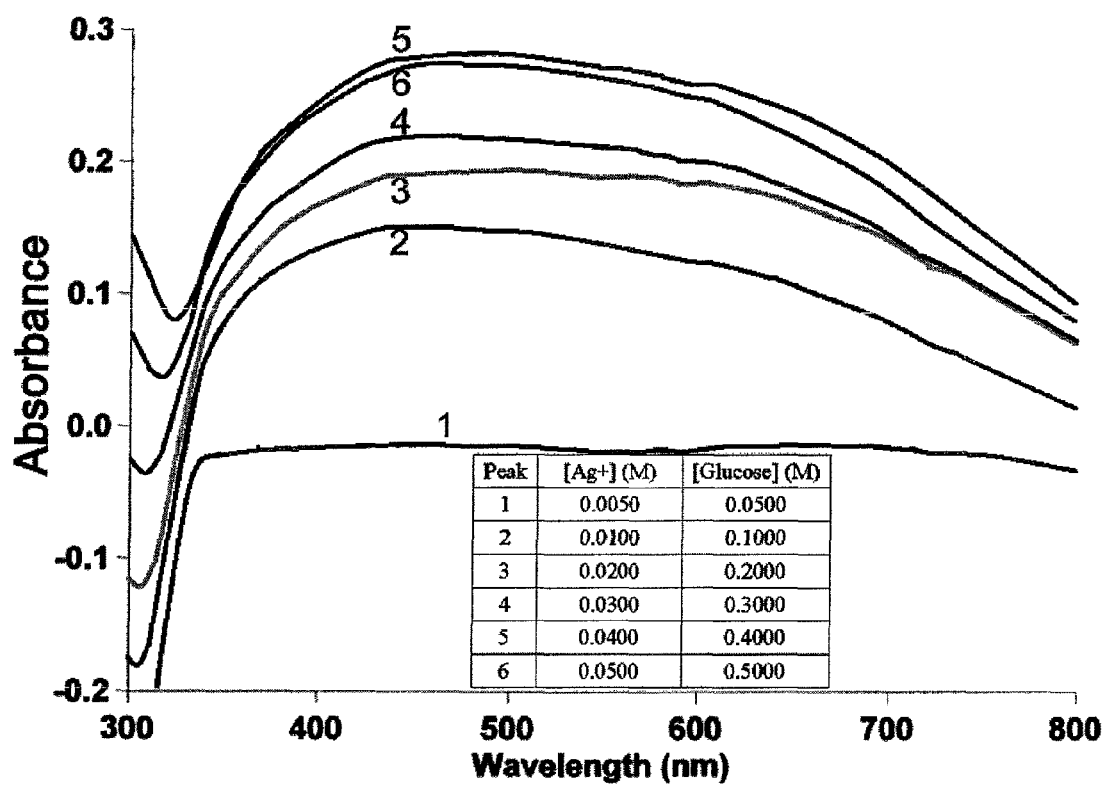
FIG. 2 is a graphical representation of the UV-visible spectra of the colloidal mixtures containing silver nanoparticles produced by mixing various concentrations of Ag$^+$ and D-glucose having a 1:10 molar ratio and after 8 s of microwaving wherein the $\lambda_{max}$ was observed at 452 nm in accordance with one embodiment of the present invention.

Nanoparticles resemble plasma wherein the free electrons form a conduction band surrounding the positively charged nuclei. A collective excitation of these electrons near the surface of the nanoparticle gives rise to Surface Plasmon Resonance. Electrons in the conduction band of a particle with a certain size and shape are limited to specific transverse oscillations via interaction with light of suitable wavelength. Therefore, metallic nanoparticles show characteristic absorption spectrum in UV-Vis region, with a Dipole Plasmon Resonance (DPR) or $\lambda_{max}$ that depends on the size of the particles. A broad absorbance peak (380-470 nm) as shown in FIG. 1A is indicative of surface plasmon absorption of metallic silver nanoparticles. To determine whether glucose concentration has any effect on nanoparticle formation, reactions were carried out with varying glucose concentrations. A 10-fold molar excess of glucose produced maximum DPR absorbance. The ratio was critical as a slight change in the molar ratio caused a significant change in absorbance as shown in FIG. 2.

Example 3

Figure 1B:
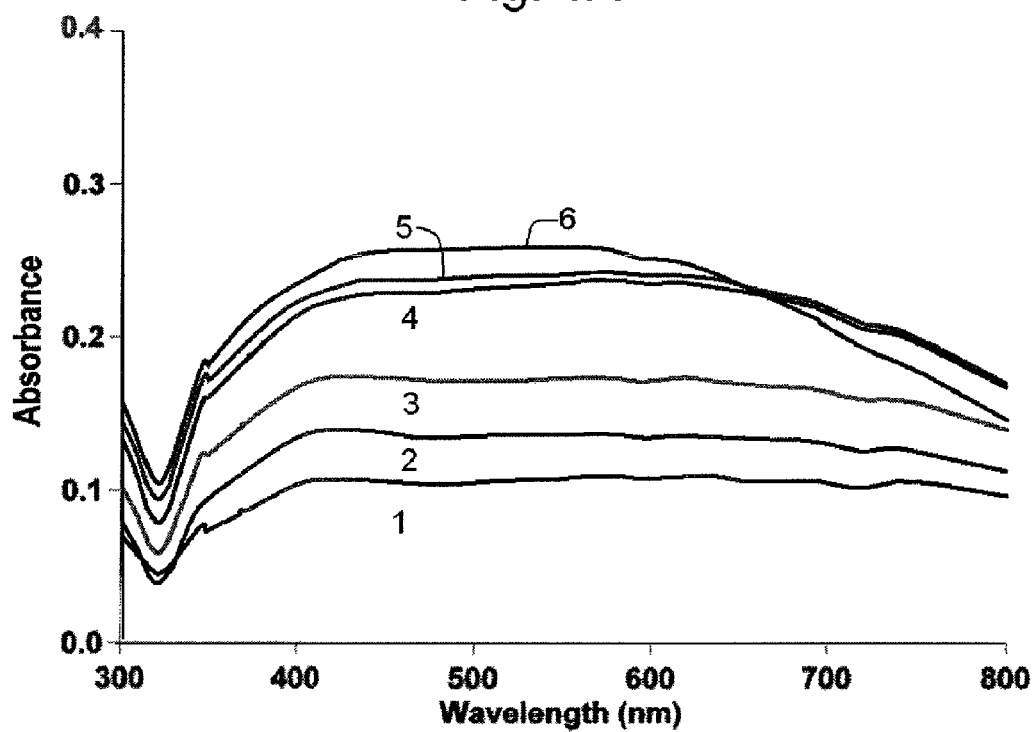
FIG. 1B is a graphical representation of the UV-visible spectra of the reaction mixtures of FIG. 1A after being subjected to an additional 10 s of microwaving wherein the spectra obtained showed a red-shift of $\lambda_{max}$ to 510 nm in accordance with one embodiment of the present invention.
Figure 1C:
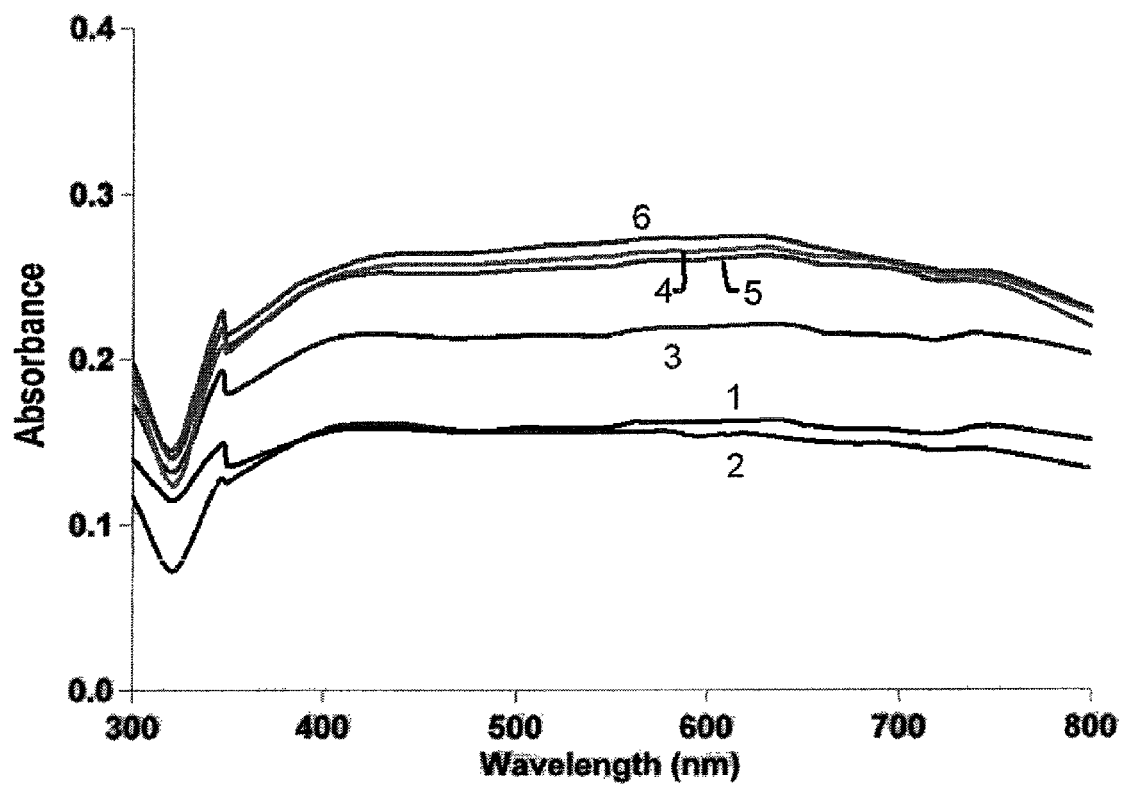
FIG. 1C is a graphical representation of the UV-visible spectra of the reaction mixtures produced in FIG. 1B after being subjected to an additional 10 s of microwaving wherein a further red-shift in $\lambda_{max}$ to 575 nm is shown in accordance with one embodiment of the present invention.

It was determined that the length of microwaving had an effect on the nanoparticles formation. An additional 10 seconds of microwaving did not result in noticeable visual differences in the color of the reaction mixtures. However, the absorbance wavelength of silver nanoparticles showed a red shift to ~435 nm as shown in FIG. 1B. This shift was due to the additional reaction time that allowed more $Ag^+$ to be reduced to $Ag^0$ atoms and nucleate thereby giving rise to larger crystalline structures that have higher absorbance wavelengths. A further 10 seconds of microwaving did not produce the same red shift on the main peak but the absorbance intensity for wavelength greater than 500 nm increased thereby indicating more aggregation as shown in FIG. 1C. Moreover, no visible aggregation was observed in the reaction tube that was left at room temperature until after 14 days had passed. This was likely due to the excess glucose in the reaction mixture that was acting both as a capping reagent and a stabilizer.

Example 4

Figure 3A:
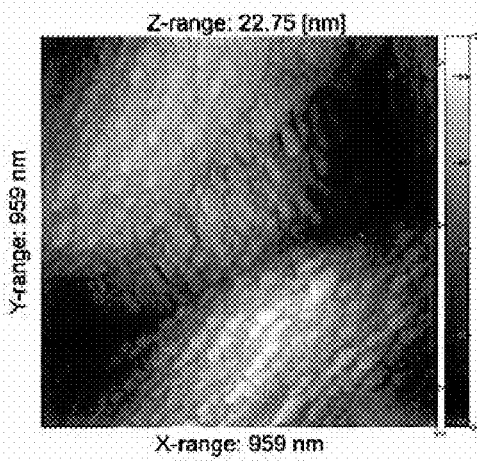
FIG. 3A is a scanning tunneling microscopy (STM) image of a portion of the silver nanoparticles produced by reduction with glucose in accordance with one embodiment of the present invention.
Figure 3B:
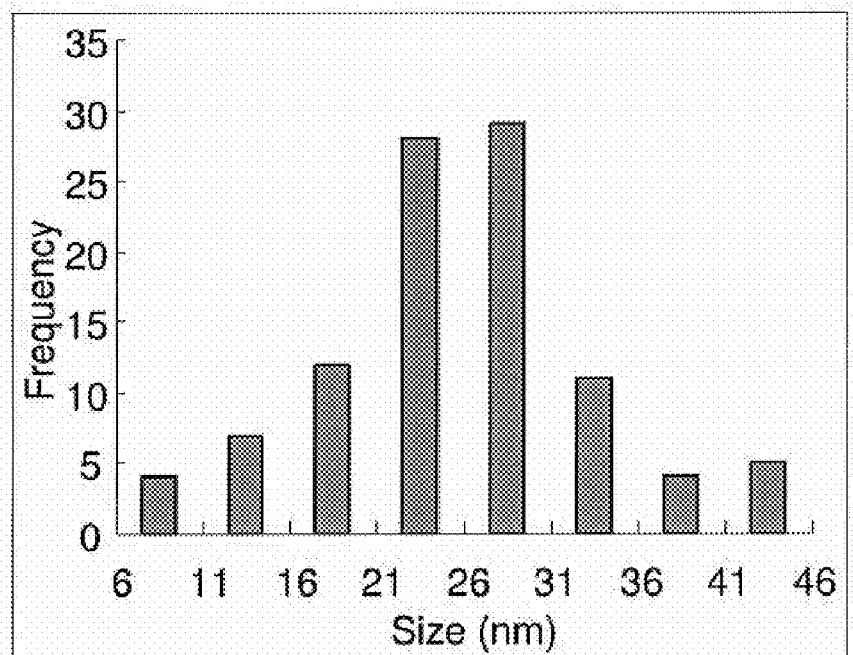
FIG. 3B is a bar chart showing the size distribution of 100 of the synthesized silver nanoparticles of FIG. 3A in accordance with one embodiment of the present invention.
Figure 4A:
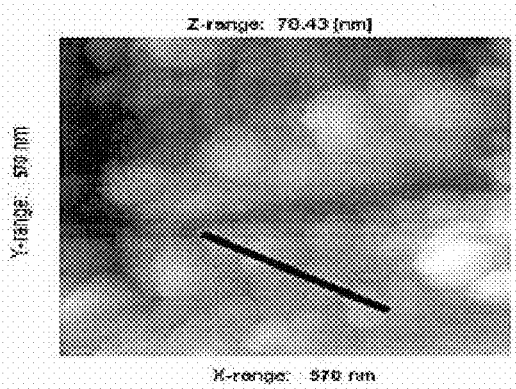
FIG. 4A is an STM image of a nanocrystallite island formed by silver nanoparticles in accordance with one embodiment of the present invention.
Figure 4B:
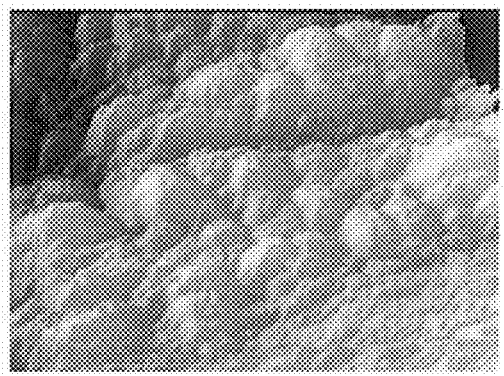
FIG. 4B is a 3-dimensional top view of the STM image of FIG. 4A in accordance with one embodiment of the present invention.
Figure 4C:
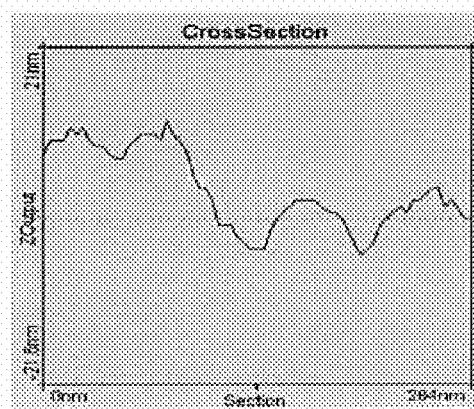
FIG. 4C is a cross-sectional view of the nanocrystallite island of FIGS. 4A and 4B indicated by the line (264 nm) in accordance with one embodiment of the present invention.

The STM data in FIG. 3A yielded a large number of nanoparticles and one hundred of these were measured for their size. The range of nanoparticle diameter along the minor axis was 5-50 nm with a mean diameter of about ~25 nm as shown in FIG. 3B. Using the Chumanov calculation for spherical silver nanoparticles, the diameter of the nanoparticles was calculated using the formula $D=0.715 \lambda_{max}-258$. The mean diameter calculated with $\lambda_{max}=452$ nm was 65 nm which corresponded to the diameter along the major axis of the oval nanoparticles (~50-70 nm) that were also synthesized. Others have reported that DPR absorbance peak between 420 nm and 450 nm produces silver nanoparticles with a mean particle size between just a few nm to 50+nm. The island platform used had surface features made up of oval silver nanoparticles with sizes ranging from ~15-75 nm and with voids therebetween. The cross-sectional view of the nanocrystallite island along the line in FIG. 4B is illustrated in FIG. 4C.

Example 5

Figure 5:
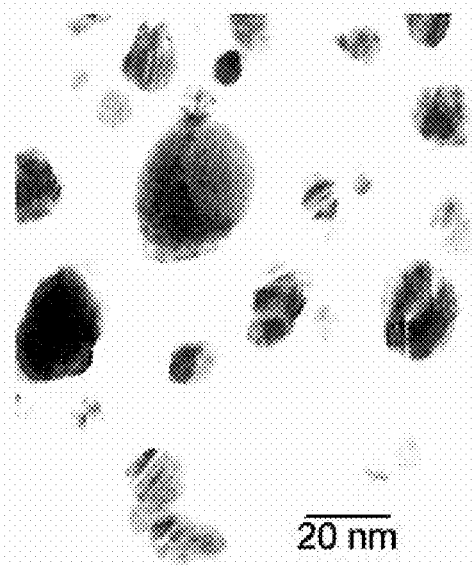
FIG. 5A is a transmission electron microscope (TEM) image of silver nanoparticles deposited on a carbon grid in accordance with one embodiment of the present invention.
FIG. 5B is a high resolution TEM image showing a single nanocrystallite with prominent fringes (shown by a pair of arrows) of regular spacing of 0.20 nm that are due to Moiré interference as the result of (200) metal silver planes in accordance with one embodiment of the present invention.
Figure 5:
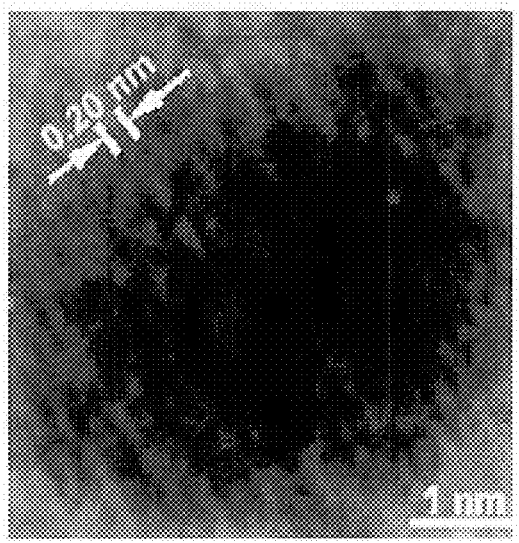

Turning to FIG. 5A, TEM revealed that the morphology of the particles synthesized using the inventive method was mostly oval with only a few displaying unsymmetrical outlines. HRTEM resolved a single silver nanocrystallite and showed the prominent fringes on the nanocrystallite that had a regular spacing of 0.20 nm due to Moiré interference as shown in FIG. 5B.

Example 6

Figure 6A:
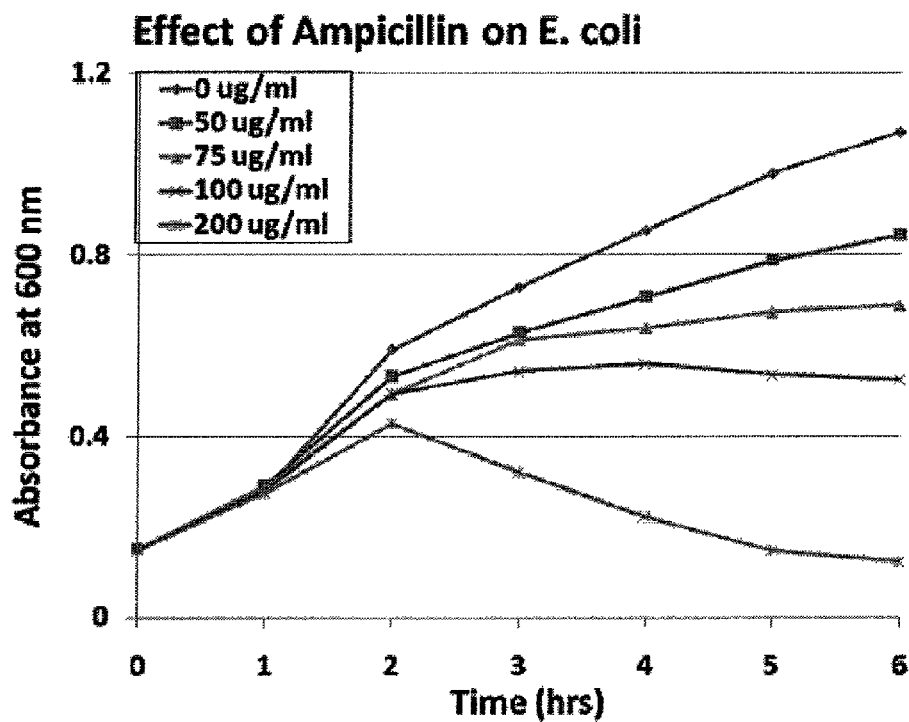
FIG. 6A is a graphical representation of bacterial cells (10$^8$ cells/ml at 0 time) in 3.5 ml LB broth wherein absorbance at 600 nm was measured every hour to monitor bacterial growth in accordance with one embodiment of the present invention.
Figure 6B:
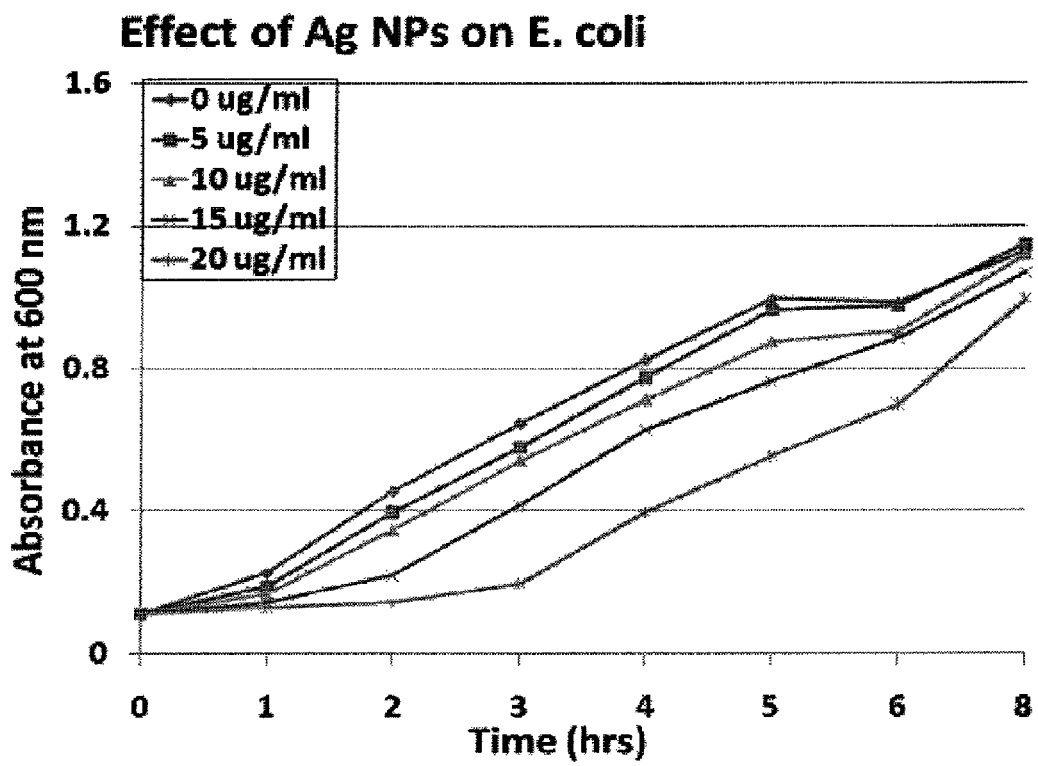
FIG. 6B is a graphical representation of silver nanoparticles at the same concentration of the bacterial cells of FIG. 6A wherein absorbance at 600 nm was measured every hour to monitor bacterial growth in accordance with one embodiment of the present invention.
Figure 6C:
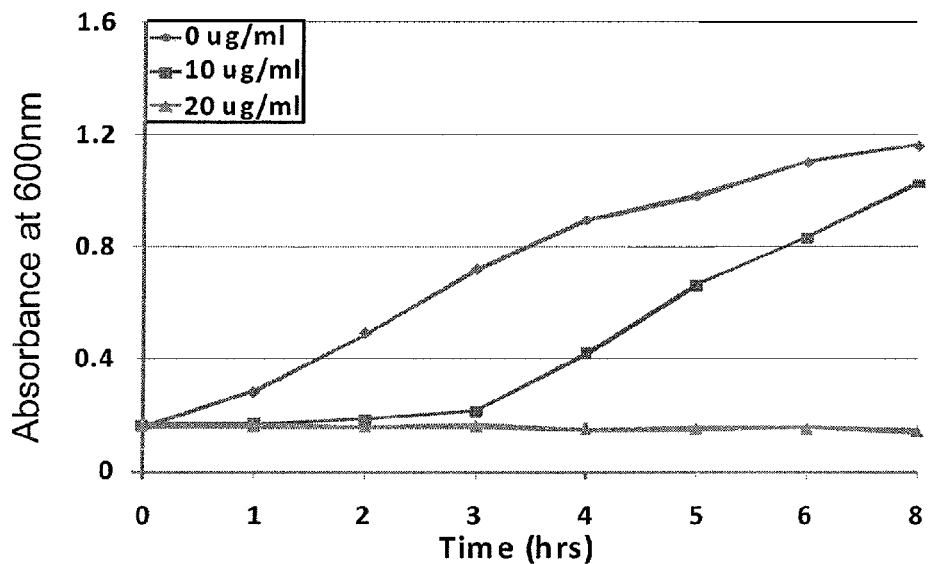
FIG. 6C is a graphical representation of bacterial cells (10$^8$ cells/ml at 0 time) in 3.5 ml LB broth wherein absorbance at 600 nm was measured every hour to monitor bacterial growth in accordance with one embodiment of the present invention.
Figure 6D:
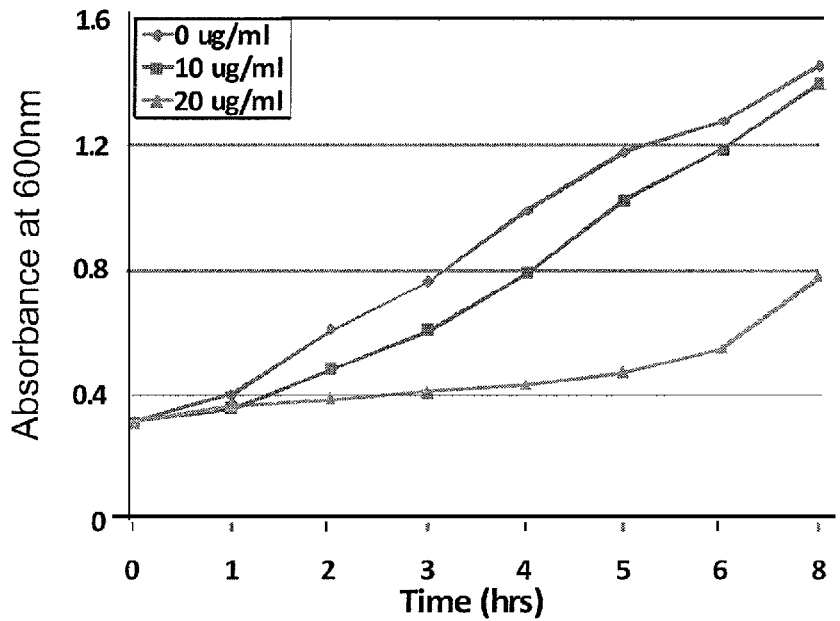
FIG. 6D is a graphical representation of bacterial cells (10$^8$ cells/ml at 0 time) in 3.5 ml LB broth wherein absorbance at 600 nm was measured every hour to monitor bacterial growth in accordance with one embodiment of the present invention.

The silver nanoparticles prepared using the method of the present invention were subsequently used to investigate antimicrobial activity. As shown in FIGS. 6A and 6B, silver nanoparticles were five times more active than antibiotic ampicillin against *E. coli*. Moreover, the silver nanoparticles were also very effective against gram-positive microbes such as *B. megaterium* and *S. epidermidis* as shown in FIGS. 6C and 6D, respectively.

Example 7

After collecting the nanoparticles, silver ions were recovered from the supernatant that contained unreacted carbohydrates and unreacted silver nitrate. In this embodiment of the inventive method, a 10-fold molar excess of sodium chloride (table salt) was added that immediately precipitated the silver ion as silver chloride (AgCl). After collecting the precipitated silver chloride, the remaining supernatant was treated with a 5-fold molar excess of NaCl. There was little to no AgCl precipitate in the second NaCl treatment thereby indicating that the supernatant was safe to dispose. The collected AgCl was dried and processed by the inventive method to recover silver ion.

Example 8

In the alternate embodiment of the inventive method described hereinabove, 0.05 M of silver nitrate was admixed with 0.5 M of sorbose in autoclaved reverse osmosis water. Immediately after mixing, the reaction mixture was microwaved in a standard household microwave oven at the highest temperature setting for about eight (8) seconds until the mixture began boiling. The reaction mixture was then placed in a centrifuge for ten minutes at 10,000 rpm in order to separate the resulting silver nanoparticles from the supernatant containing the unreacted sorbose and unreacted silver nitrate. After separation and collection, the silver nanoparticles were washed twice with autoclaved reverse osmosis water and resuspended in autoclaved reverse osmosis water until the desired concentration was reached. The remaining supernatant was treated with an excess of sodium chloride and processed to recover silver ions therefrom. This reaction was repeated four additional times using different sugars, namely, lactose, sucrose, maltose and ribose.

Example 9

Figure 7:
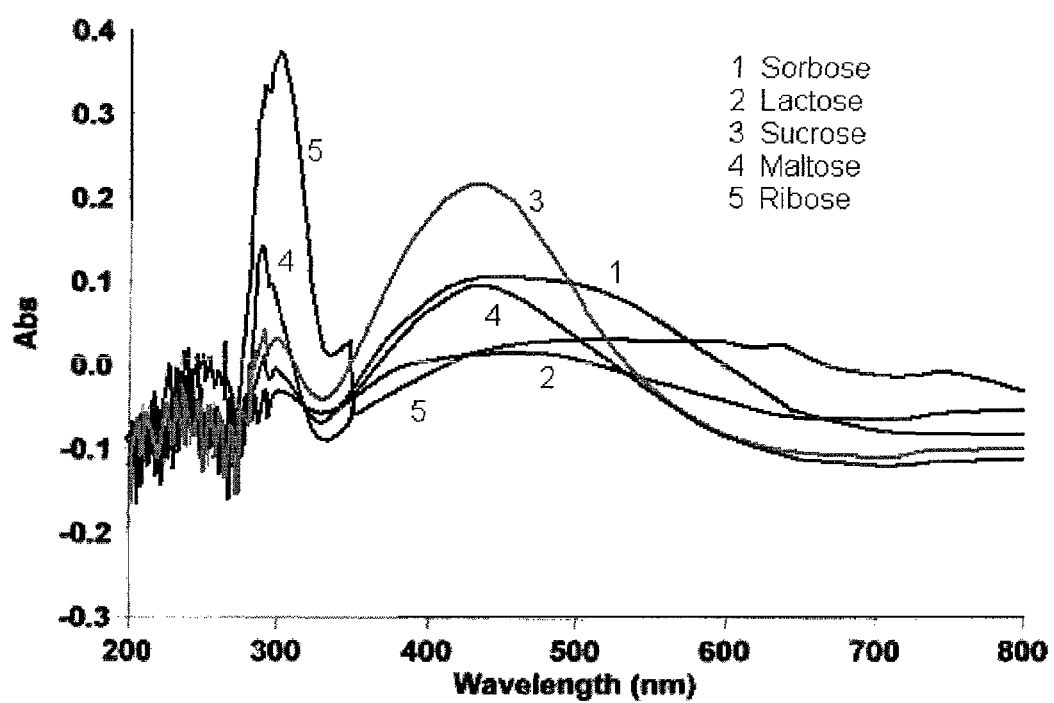
FIG. 7 is a graphical representation of the UV-visible spectra of colloidal mixtures containing silver nanoparticles wherein different $\lambda_{max}$ is observed in conjunction with the use of different sugars: sucrose at 430 nm, lactose at 460 nm, ribose at 300 nm, and glucose at 452 nm providing for an alternate method for the detection and identification of sugars.

To detect and/or identify the different sugars used, absorbance of the five different reaction mixtures of Example 8 was measured as shown in FIG. 7. Different $\lambda_{max}$ was observed for each of the different sugars: sucrose at 430 nm, lactose at 460 nm, and ribose at 300 nm. With glucose at 452 nm used as a standard, the different sugars were easily detected and identified.

Example 10

Figure 8:
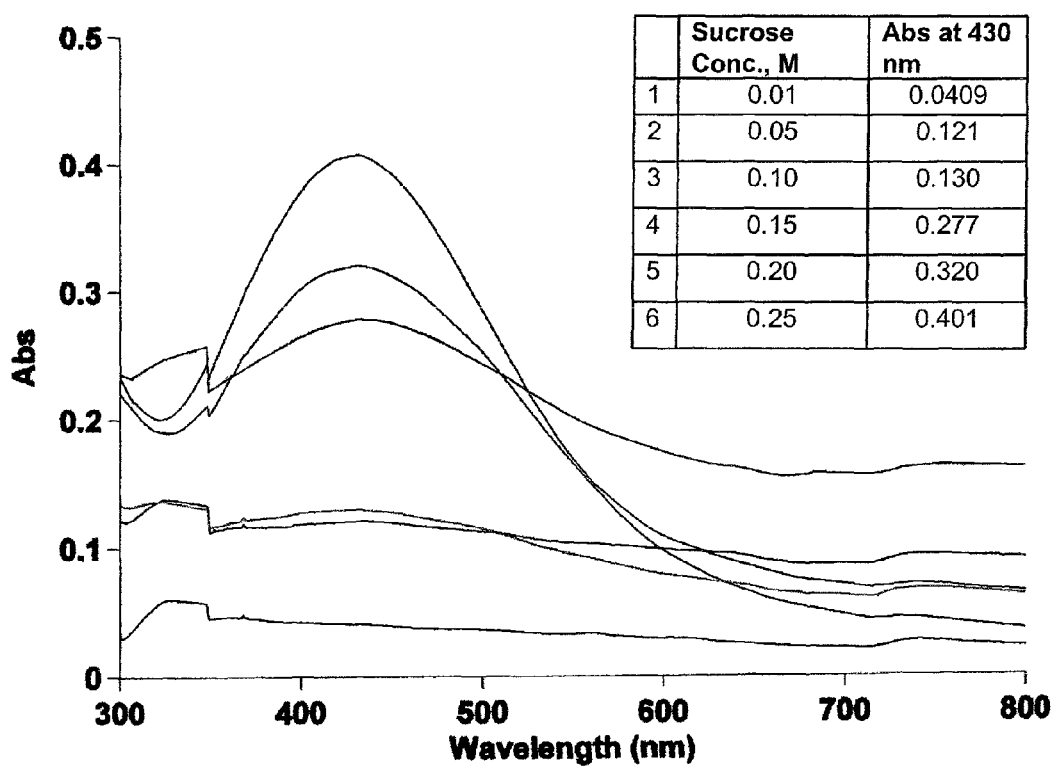
FIG. 8 is a graphical representation of the UV-visible spectra of colloidal mixtures containing silver nanoparticles wherein different concentrations of sucrose as shown in the inset table and absorbance at 430 nm were measured.

To determine whether different concentrations of sucrose had any effect on nanoparticle formation, reactions were carried out with varying sucrose concentrations as shown in the inset table of FIG. 8 and the absorbance at 430 was measured. A linear relationship was established between measured $A_{430}$ with sucrose concentration in accordance with the Beer-Lambert law thereby indicating that it could be used to measure sucrose concentration in solutions. Since sucrose is a non-reducing sugar as compared to glucose, fructose, ribose, lactose and the like, this result was unexpected.

Example 11

Figure 9:
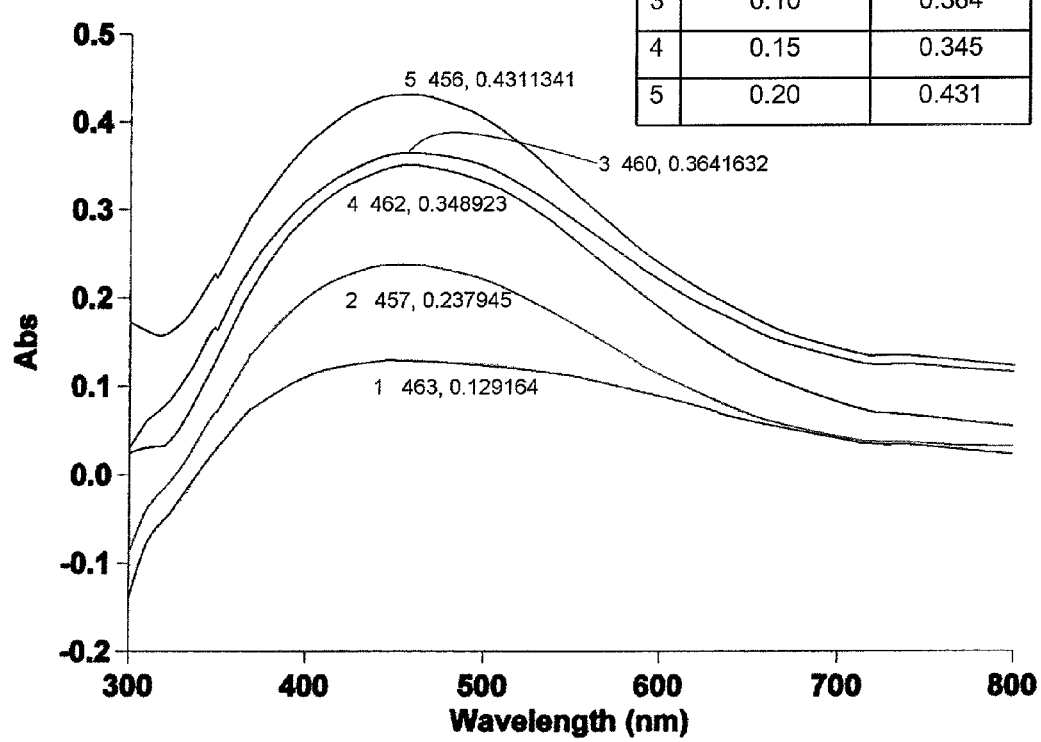
FIG. 9 is a graphical representation of different concentrations of lactose shown in the inset table and absorbance at 460 nm were measured.

To determine whether different concentrations of lactose had any effect on nanoparticle formation, reactions were carried out with varying lactose concentrations as shown in the inset table of FIG. 9 and the absorbance at 460 was measured. A linear relationship was established between measured $A_{460}$ with lactose concentration in accordance with the Beer-Lambert law thereby indicating that it could be used to measure sucrose concentration in solutions such as milk.

Having described the invention in detail, those skilled in the art will appreciate that modifications may be made of the invention without departing from the spirit and scope thereof. Therefore, it is not intended that the scope of the invention be limited to the specific embodiments described. Rather, it is intended that the appended claims and their equivalents determine the scope of the invention.

What is claimed is:

1. A method of producing silver nanoparticles comprising the steps of:
    providing an aqueous solution containing a quantity of silver nitrate and a quantity of a carbohydrate reductant;
    heating said solution in a household microwave oven;
    separating and collecting silver nanoparticles from said solution; and
    recovering unreacted silver ions from said solution.

2. The method of claim 1 wherein said silver nitrate and said carbohydrate reductant are present in a 1:10 molar ratio.

3. The method of claim 1 wherein said carbohydrate reductant is selected from the group consisting of polyhydroxy aldehydes, polyhydroxy ketones, and mixtures thereof.

4. The method of claim 1 wherein said carbohydrate reductant is selected from the group consisting of glucose, sucrose, lactose, fructose, galactose, ribose, and mixtures thereof.

5. The method of claim 1 wherein said carbohydrate reductant is selected from the group consisting of high fructose corn syrup, sucrose syrup, dextrose, and mixtures thereof.

6. The method of claim 1 wherein said silver nanoparticles each have a size of generally equal to or less than 200 nm.

7. The method of claim 1 wherein said heating step is performed until said solution reaches boiling point.

8. The method of claim 7 wherein said solution is heated in said microwave oven for a period of from about 1-30 seconds.

9. The method of claim 1 wherein said silver nanoparticles have antimicrobial characteristics.

10. A method of producing silver nanoparticles comprising the steps of:
   providing an aqueous solution containing a quantity of silver nitrate and a quantity of a carbohydrate reductant;
   heating said solution in a household microwave oven;
   separating and collecting silver nanoparticles from said solution wherein said silver nanoparticles each have a size of from about 20-100 nm; and
   recovering unreacted silver ions from said solution.

11. A method of producing silver nanoparticles comprising the steps of:
   providing an aqueous solution containing a quantity of silver nitrate and a quantity of a carbohydrate reductant;
   heating said solution until it reaches boiling point in a household microwave oven for a period of from about 2-10 seconds;
   separating and collecting silver nanoparticles from said solution; and
   recovering unreacted silver ions from said solution.

12. A method of producing silver nanoparticles comprising the steps of:
   providing an aqueous solution containing a quantity of silver nitrate and a quantity of a carbohydrate reductant;
   heating said solution in a household microwave oven;
   separating and collecting silver nanoparticles from said solution; and
   recovering unreacted silver ions from said solution by adding about a 10-fold molar excess of sodium chloride to said unreacted silver nitrate and unreacted carbohydrate reductant.

13. The method of claim 12 wherein said recovering step further comprises collecting the resulting precipitated silver chloride.

14. The method of claim 13 wherein said recovering step further comprises drying said collected silver chloride.

15. A method of producing silver nanoparticles having a size of about 200 nm or less comprising the steps of:
   providing an aqueous solution containing about a 1:10 molar ratio of silver nitrate to a carbohydrate reductant selected from the group consisting of polyhydroxy aldehydes, polyhydroxy ketones, and mixtures thereof;
   heating said solution for about two to ten seconds in a microwave oven;
   separating and collecting precipitated silver nanoparticles from said solution;
   adding about a 10-fold molar excess of sodium chloride to unreacted silver nitrate and unreacted carbohydrate reductant remaining in a supernatant of said solution;
   collecting the resulting precipitated silver chloride; and
   drying said collected silver chloride.

16. A method of producing nanoparticles comprising the steps of:
   providing an aqueous solution containing a quantity of a metal ion source and a quantity of a carbohydrate reductant;
   heating said solution in a household microwave oven;
   separating and collecting metal nanoparticles from said solution; and
   recovering unreacted metal ion source from said solution.

17. The method of claim 16 wherein said metal ion source is selected from the group consisting of silver, gold, cobalt and nickel.

18. A method of measuring sugar concentrations in solutions comprising the steps of:
   providing an aqueous solution containing a quantity of a metal ion source and a quantity of a sugar selected from the group consisting of sucrose, sorbose, lactose, maltose, and ribose;
   heating said solution in a microwave oven;
   separating and collecting metal nanoparticles from said solution;
   measuring the absorbance of said sugar to determine the concentration of said sugar.

* * * * *